(12) United States Patent
Bridge et al.

(10) Patent No.: US 8,166,586 B2
(45) Date of Patent: May 1, 2012

(54) REMOVABLE PALLETS AND PATIENT TABLES FOR MEDICAL SYSTEMS

(75) Inventors: William J. Bridge, Delafield, WI (US); Robert Grams, Waukesha, WI (US); Thomas K. S. Schaefer, Germantown, WI (US); Eric Stepanovich, Pewaukee, WI (US); Scott Wollenweber, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 31 days.

(21) Appl. No.: 12/641,558

(22) Filed: Dec. 18, 2009

(65) Prior Publication Data

US 2011/0145991 A1 Jun. 23, 2011

(51) Int. Cl.
*A47B 13/00* (2006.01)
(52) U.S. Cl. ............................. 5/601; 5/600; 600/415
(58) Field of Classification Search .............. 5/600, 601, 5/81.1 HS; 378/209, 62; 600/415
See application file for complete search history.

(56) References Cited

U.S. PATENT DOCUMENTS

| 4,688,278 | A | * | 8/1987 | Van Aspert | ...................... | 5/601 |
| 5,475,884 | A | * | 12/1995 | Kirmse et al. | ................... | 5/601 |
| 6,782,571 | B1 | | 8/2004 | Josephson et al. | | |
| 7,264,396 | B2 | | 9/2007 | Jährling | | |
| 7,467,004 | B2 | * | 12/2008 | Calderon et al. | ............. | 600/415 |
| 7,869,858 | B2 | * | 1/2011 | Calderon et al. | ............. | 600/415 |
| 7,874,030 | B2 | * | 1/2011 | Cho et al. | .......................... | 5/601 |
| 2002/0129446 | A1 | * | 9/2002 | Heinold et al. | ................... | 5/601 |
| 2007/0003022 | A1 | * | 1/2007 | Hornig | ......................... | 378/209 |
| 2007/0191706 | A1 | | 8/2007 | Calderon et al. | | |
| 2009/0056023 | A1 | * | 3/2009 | Calderon et al. | .................. | 5/601 |
| 2009/0217456 | A1 | * | 9/2009 | Lempen et al. | ................... | 5/601 |

OTHER PUBLICATIONS

Patient Transporter Transmobil 2 Translife; Maquet GmbH & Co. KG, Getinge Group, www.maquet.com; Dec. 2007, 16 pgs.

\* cited by examiner

*Primary Examiner* — Robert G Santos
*Assistant Examiner* — Brittany Wilson
(74) *Attorney, Agent, or Firm* — The Small Patent Law Group; Dean D. Small

(57) ABSTRACT

A removable pallet configured to be mounted to a patient table. The patient table has a table surface adapted to support patients thereon during a medical procedure or imaging session. The removable pallet includes a support body having a runway configured to slidably engage a transfer board carrying a patient. The support body extends along a longitudinal axis and is configured to be mounted over the table surface of the patient table. The removable pallet also includes a coupling device that is configured to removably couple the support body and the patient table. The coupling device secures the support body over the table surface to permit the transfer board to be moved onto the patient table.

19 Claims, 13 Drawing Sheets

REMOVABLE PALLETS AND PATIENT TABLES FOR MEDICAL SYSTEMS

BACKGROUND OF THE INVENTION

The subject matter disclosed herein relates generally to medical systems and more particularly, to patient tables that support a patient during an imaging session or another medically related event.

Patients can be imaged using a wide variety of different imaging technologies. Medical imaging systems may include one or more different imaging modalities, such as, magnetic resonance imaging (MRI), computer tomography (CT), positron emission tomography (PET), single photon emission computed tomography (SPECT), x-ray imaging, and others. Imaging systems typically include field-of-views (FOVs) where a patient is positioned to be imaged. On some occasions, a patient is imaged using multiple modalities. For example, x-ray imaging can be used to guide invasive devices and MRI can be used to monitor the results of therapy in the surrounding tissues. Different imaging systems may have patient tables with different characteristics and/or dimensions. Furthermore, patient tables of various designs may be found in a medical environment.

In some applications, it may be necessary to move the patient from one location to another or to move the patient in a manner that reduces anatomical movement and/or disruption of the patient. In some known systems, a patient may be transferred from a first imaging system (e.g., x-ray imaging system) to a second imaging system (MR imaging system) using a transfer board. More specifically, the patient rests on a transfer board that is carried by a transporter or gurney. The gurney is configured to move to different locations. When the gurney is docked with the first imaging system, the transfer board may be moved axially along a patient table of the first imaging system to position the patient within the FOV of the first imaging system. After the imaging session of the first imaging system, the patient may be moved onto the gurney and then transported to the second imaging system. The patient is then positioned within the second imaging system by moving the transfer board onto a patient table of the second imaging system.

However, the patient tables of such first and second imaging systems may be specially designed to receive the transfer board. In such cases, the specially-designed patient tables may not be suitable for standard imaging sessions where, for example, the patient independently mounts the patient table herself or is picked up and placed onto the table. Accordingly, it may be necessary to use two different imaging systems of the same type that have differently configured patient tables. This adds costs and also reduces the amount of available space within a building due to storage of multiple tables.

BRIEF DESCRIPTION OF THE INVENTION

In one embodiment, a removable pallet configured to be mounted to a patient table is provided. The patient table has a table surface adapted to support patients thereon during a medical procedure or imaging session. The removable pallet includes a support body having a runway configured to slidably engage a transfer board carrying a patient. The support body extends along a longitudinal axis and is configured to be mounted over the table surface of the patient table. The removable pallet also includes a coupling device connected to the support body. The coupling device is configured to removably couple the support body and the patient table. The coupling device secures the support body over the table surface to permit the transfer board to be moved onto the patient table.

In another embodiment, a method of transferring a patient onto a patient table is provided. The method includes providing a patient table that extends along a longitudinal axis and mounting a removable pallet onto the patient table. The removable pallet extends along the longitudinal axis over the patient table. The method also includes removably securing the removable pallet to the patient table. The removable pallet including a runway configured to slidably engage a transfer board having a patient thereon.

In yet another embodiment, a reconfigurable imaging table for a medical imaging system is provided. The imaging table includes a cradle with a table surface extending along a longitudinal axis. The table surface is adapted to support a patient thereon during an imaging session. The imaging table also includes a removable pallet that is configured to be mounted to the cradle. The removable pallet has a runway configured to slidably engage a transfer board. The removable pallet extends along the longitudinal axis when mounted to the cradle. The imaging table also includes a coupling device that is connected to the removable pallet. The coupling device is configured to removably couple the removable pallet and the cradle. The coupling device secures the removable pallet to the cradle to permit the transfer board to be moved onto the runway of the removable pallet.

DETAILED DESCRIPTION OF THE INVENTION

The foregoing summary, as well as the following detailed description of certain embodiments of the present invention, will be better understood when read in conjunction with the appended drawings. As used herein, an element or step recited in the singular and proceeded with the word "a" or "an" should be understood as not excluding plural of said elements or steps, unless such exclusion is explicitly stated. Furthermore, references to "one embodiment" or "an embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Figure 1:
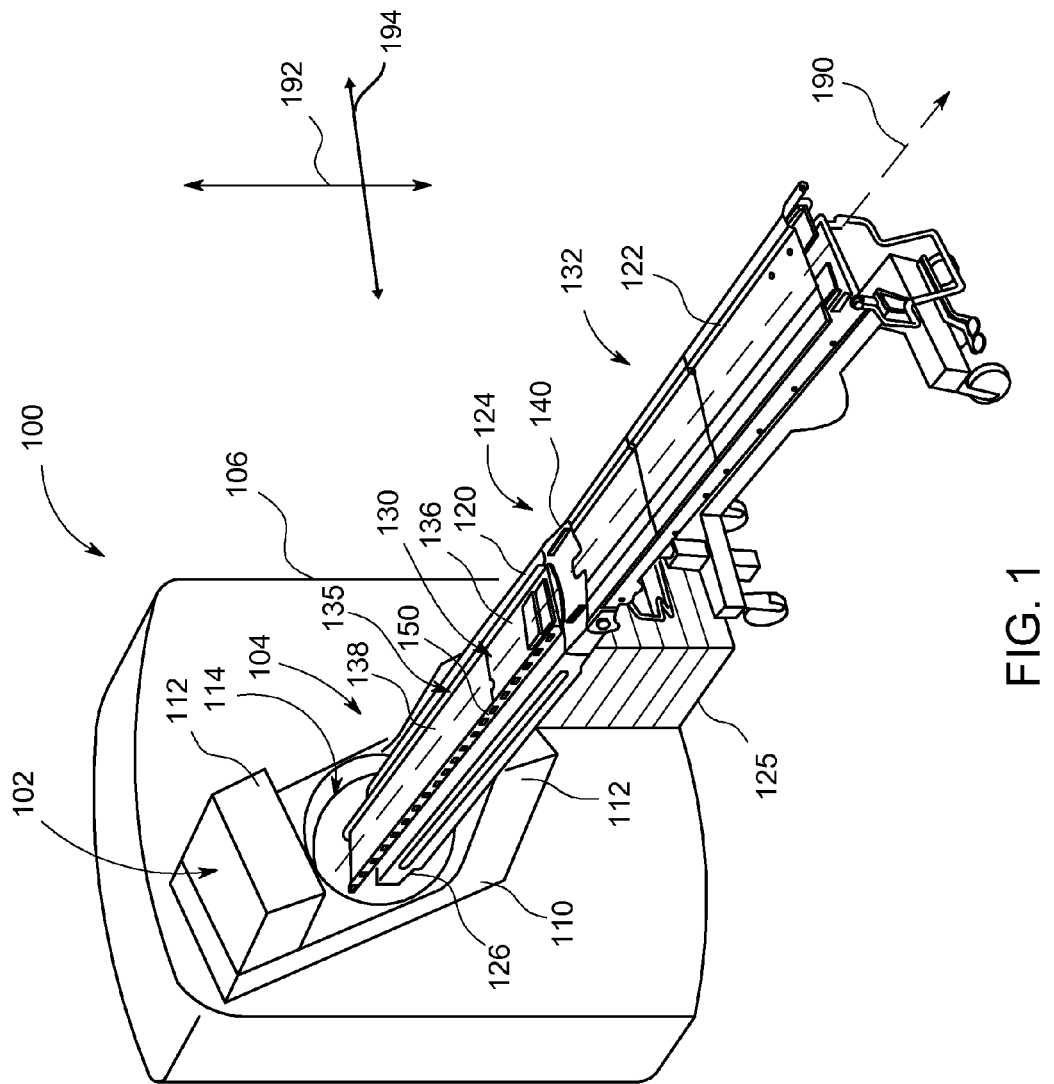
FIG. 1 is a perspective view of an exemplary medical imaging system showing a patient table formed in accordance with various embodiments.

FIG. 1 is a perspective view of an exemplary medical imaging system 100. The imaging system 100 may be any type of imaging system, including a multi-modality imaging system. For example, the imaging system 100 may include one or more types of imaging modality units, such as a Positron Emission Tomography (PET) modality unit, a Single Photon Emission Computed Tomography (SPECT) modality unit, a Computed Tomography (CT) modality unit, an ultrasound modality unit, a Magnetic Resonance Imaging (MM) modality unit, an X-Ray radiography or fluoroscopy modality unit, and/or any other modality unit capable of generating images of a region of interest (ROI) of a patient. In particular embodiments, the imaging system 100 is a medical imaging system. The various embodiments are not limited to medical imaging systems for imaging human subjects, but may include, for example, veterinary systems. As used herein, the term "patient" may refer to a human patient or any other animal.

Referring to FIG. 1, the imaging system 100 includes an imaging modality unit 102 that enables the imaging system 100 to scan a patient (not shown) in a first modality positioned at a field-of-view (FOV) 104. In the exemplary embodiment, the imaging modality unit 102 is configured for nuclear medicine (NM) imaging. However, the imaging modality unit 102 may be various types of imaging modality units, such as those described above. Furthermore, the imaging system 100 may include multiple imaging modality units. In the illustrated embodiment, the imaging system 100 includes a gantry 106 that is associated with an NM imaging system. The gantry 106 includes a rotor 110 that supports one or more NM cameras 112. The NM cameras 112 may be, for example, gamma cameras, SPECT detectors, and/or PET detectors. The rotor 110 is configured to rotate the NM cameras 112 about a longitudinal or examination axis 190 that may extend through a bore 114 of the imaging system 100. The bore 114 extends through the gantry 106 along the longitudinal axis 190. The bore 114 is sized and shaped to allow a patient (not shown) to be moved into and out of the bore 114.

The imaging system 100 may also include an imaging or patient table 120 that is configured to hold a patient in a desired or predetermined position within the FOV 104. The patient table 120 extends along the longitudinal axis 190 between a first or mating end 124 and a second or bore end 126 located proximate to the FOV 104. The patient table 120 may be supported by a pedestal or table base 125. In some embodiments, the table base 125 is configured to selectively move the patient table 120 to desired elevations in a direction along a vertical axis 192. Furthermore, in some embodiments, the table base 125 may be configured to selectively move the patient table 120 along the longitudinal axis 190. The patient table 120 may also be configured to move laterally or side-to-side (e.g., left-to-right) along a lateral axis 194.

The patient table 120 as shown in FIG. 1 is reconfigurable and includes a removable pallet 130 mounted thereon. The removable pallet 130 may be similarly sized and shaped as a cradle 442 (FIG. 9) of the patient table 120 and may extend along the longitudinal axis 190. The removable pallet 130 may include a runway 150 that is configured to receive and slidably engage a transfer board 122.

In particular embodiments, the removable pallet 130 includes a support body 135 having multiple body sections 136 and 138. The body sections 136 and 138 couple together to form the support body 135 of the removable pallet 130. The patient table 120 may be used to image a region of interest (ROI) of the patient when the patient lies on the cradle 442 or, separately, the removable pallet 130. As will be described in greater detail below, the removable pallet 130 is removably coupled to the patient table 120 to secure the removable pallet 130 thereto. Accordingly, embodiments described herein include reconfigurable patient tables or imaging systems that may be adapted as desired or needed. For example, the patient tables or imaging systems may be configured for different patients.

As used herein, the term "removable" when used to modify "couple," "engage," "mount," or "secure" means the components may be readily separated without destroying or significantly damaging either component. Two components are readily separable when the components can be separated without significant effort and within a reasonable period of time for its intended use. For example, it may be necessary for an operator of the imaging system 100 to frequently mount and demount the removable pallet 130 to the patient table 120 within a day or shift. However, other components may be permanently or semi-permanently affixed to one another. As used herein, when two components are affixed, the components may or may not be separable from each other. However, affixed components are typically not separable without significant effort and/or within a reasonable period of time. For example, whereas removably coupled components may be configured to be separated multiple times in one day, affixed components are intended to remain coupled during normal usage of the patient table. As described below, a coupling device may be affixed to another component such that the coupling device remains coupled to the component when the removable pallet 130 is mounted to and demounted from the patient table 120.

As shown in FIG. 1, the patient may be moved to different locations (e.g., different imaging systems) by a gurney or transporter 132. The transporter 132 is configured to hold and slidably engage the transfer board 122. In some embodiments, the patient table 120 includes a docking interface 140 located proximate to the mating end 124. The docking interface 140 is configured to facilitate transferring the transfer board 122 between the patient table 120 and the transporter 132. Furthermore, the docking interface 140 may be configured to removably engage the transporter 132 such that the transporter 132 does not inadvertently move away from the patient table 120.

As used herein, the term "slidably engage" may include the transfer board engaging at least one of guiding features of the runway and a surface of the removable pallet. For example, the transfer board may glide or slide along the pallet surface or surfaces of guiding features, such as those described below. The surfaces may be reduced friction surfaces, such as Teflon®. In various embodiments, the runway may include (a) only the pallet surface, (b) only guiding features as described below, or (c) the pallet surface and guiding features. The runway may include additional features or components that facilitate the removable pallet in engaging the transfer board. In alternative embodiments, the runway is only a flat surface and the transfer board is directed or guided by other means.

The runway 150 is configured to receive the transfer board 122. In the illustrated embodiment, a front end of the transfer board 122 is loaded onto the removable pallet 130 through the docking interface 140 and moved in an axial direction along the longitudinal axis 190. However, in alternative embodiments, the transfer board 122 may be laterally loaded onto the removable pallet 130. For example, the transfer board 122 may be positioned along a side of the patient table 120 and laterally loaded onto the removable pallet 130. In such cases, the runway 150 may be particularly configured to receive that transfer board 122 in a lateral direction (i.e., in a direction that is substantially perpendicular to the longitudinal axis 190). For example, the guiding features may be configured to receive the transfer board from the side of the patient table 120. The guiding features may engage front and back ends or edges of the transfer board 122.

Although the illustrated embodiment includes a patient table of a medical imaging system, alternative embodiments may include patient tables used for different medical purposes where it may be desired to transfer a patient without disrupting the patient or without anatomical movement. For example, the patient table may be a surgical table where a patient is delivered for surgery. As another example, the patient table may be located within an emergency room of a hospital. In such alternative embodiments, the removable pallet may include various features that are suitable for its intended purpose. Accordingly, the following description of the patient table 120 is not intended to limit the patient table 120 to only being used with medical imaging systems.

Figure 2:
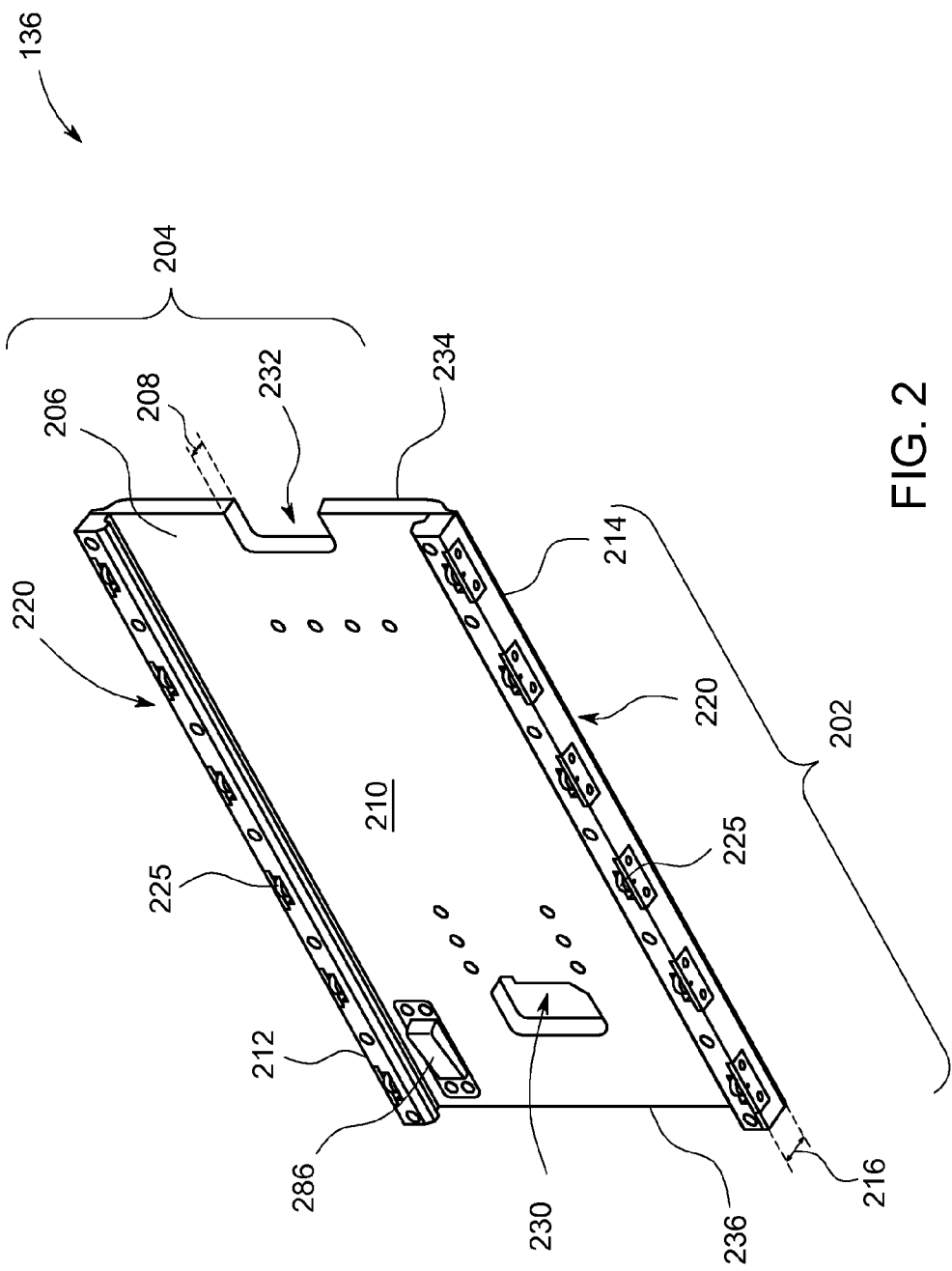
FIG. 2 is a perspective view of a body section that may be used to form a removable pallet in accordance with various embodiments.
Figure 3:
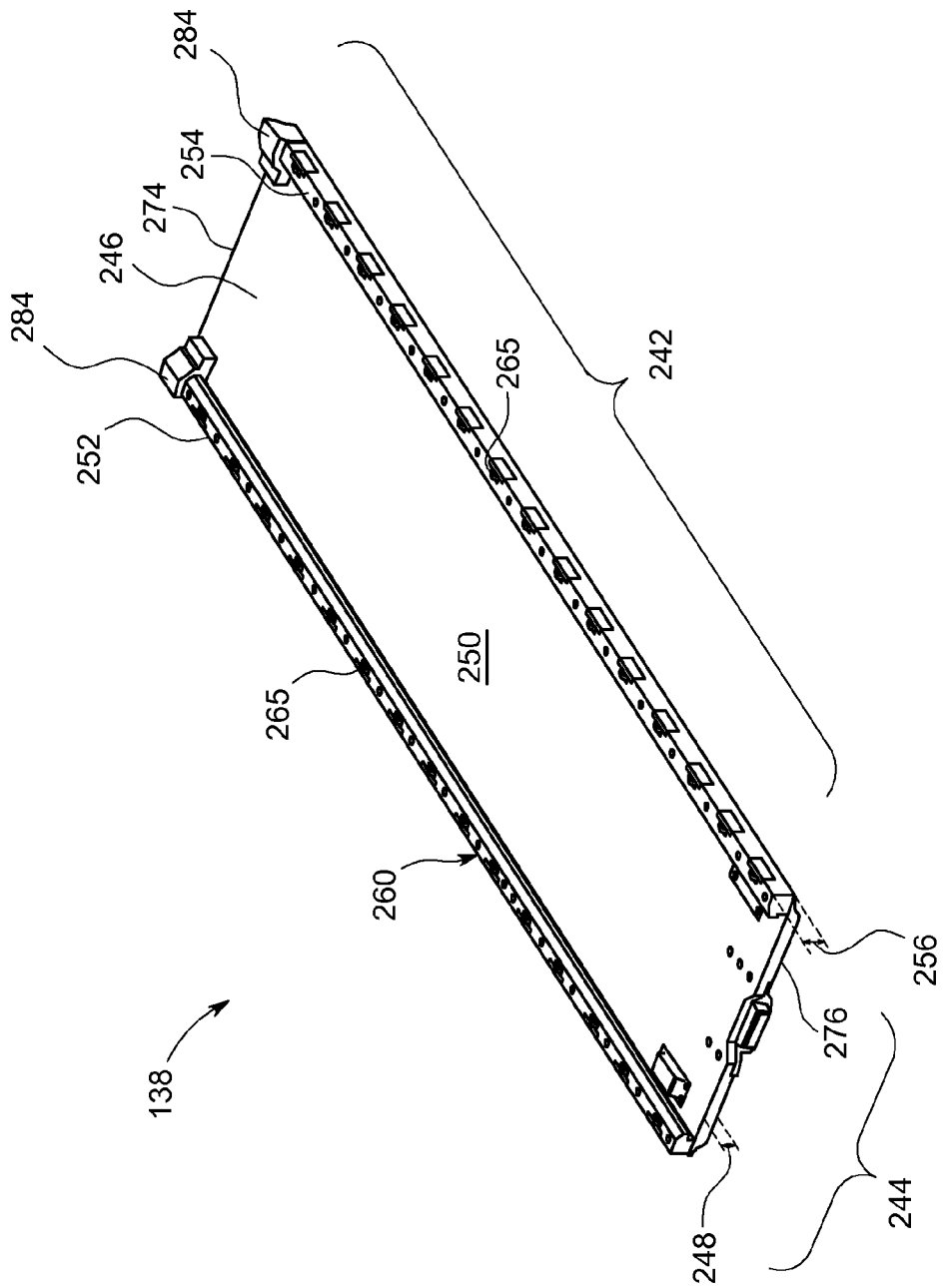
FIG. 3 is a perspective view of another body section that may be coupled to the body section shown in FIG. 2 to form the removable pallet.

FIGS. 2-5 illustrate various components that may be used to form the removable pallet 130 (FIG. 1). FIGS. 2 and 3 illustrate perspective views of the first and second body sections 136 and 138, respectively, that are configured to be coupled together to form the support body 135 (FIG. 1) of the removable pallet 130. With respect to FIG. 2, the body section 136 includes a length 202 that is configured to extend along the longitudinal axis 190 (FIG. 1) and a width 204 that is sized to receive the transfer board 122 (FIG. 1). In the illustrated embodiment, the body section 136 includes a body pad 206 having a substantially rectangular shape and extends substantially the length 202 and the width 204 and also includes a thickness 208. The thickness 208 may be uniform across the width 204 or may vary. In alternative embodiments, the body section 136 or the body pad 206 may have different sizes and shapes. The body section 136 also includes a support surface 210 that is sized and shaped to permit the transfer board 122 to move therealong. The support surface 210 may also be sized and shaped to support the transfer board 122 when moved therealong. For example, the support surface 210 may have a contour that complements a bottom of the transfer board 122.

In some embodiments, the removable pallet 130 includes at least one guiding feature 212 or 214 that facilitates directing or guiding the transfer board 122. The guiding features may be, for example, rails, slots, tracks, and the like, that extend along the runway 150 in a direction along the longitudinal axis 190. The guiding feature(s) 212 or 214 may engage the transfer board 122 and facilitate directing the transfer board 122 to an axial location along the patient table 120 (FIG. 1). For example, as shown in FIG. 2, the guiding features 212 or 214 may include a pair of spaced apart board rails located on the body section 136. The guiding features 212 and 214 have a height 216 that projects away from the support surface 210. Also shown, the guiding features 212 and 214 include respective mating edges 220 that may engage the transfer board 122. In some embodiments, the mating edges 220 include rollers 225 that reduce friction between the transfer board 122 and the removable pallet 130. The rollers 225 may be aligned and spaced apart along the longitudinal axis 190. In the illustrated embodiment, the rollers 225 are shown as wheels that rotate bi-directionally about an axis. In other embodiments, the rollers 225 may be ball bearings or other rotatable/movable components that reduce friction and facilitate moving the transfer board 122. Furthermore, in the illustrated embodiment, the guiding features 212 and 214 are separate components that are attached to the body pad 206. However, in other embodiments, the guiding features may be integrally formed with the body pad 206.

As shown in FIG. 2, the body section 136 may include one or more openings. For example, the body section 136 has a hole 230 located proximate to a section end 236 and a cut-out 232 located proximate to a section end 234 of the body section 136. The cut-out 232 may open to the section end 236. The hole 230 and the cut-out 232 may provide access for an operator or tool to facilitate mounting and demounting the body section 136 to the patient table 120. Also shown in FIG. 2, the body section 136 may include a safety latch 286 located proximate to the section end 236. The safety latch 286 may be configured to prevent the transfer board 122 from inadvertently sliding off the removable pallet 130. The safety latch 286 may be required to be manually depressed by a technician or tool before the transfer board 122 is removed.

Similarly, as shown in FIG. 3, the body section 138 includes a length 242 that is configured to extend along the longitudinal axis 190 (FIG. 1) and a width 244 that is sized to receive the transfer board 122 (FIG. 1). In the illustrated embodiment, the body section 138 includes a body pad 246 having a substantially rectangular shape and extends substantially the length 242 and the width 244 and also includes a thickness 248. However, the body section 138 or the body pad 246 may have different sizes and shapes. Also shown, the body section 138 includes a support surface 250 that is sized and shaped to permit the transfer board 122 to move therealong. The support surface 250 may also be sized and shaped to support the transfer board 122 when moved therealong. The support surface 250 may have a contour that complements a bottom of the transfer board 122. Also shown, the body section 138 may include a safety latch 287 that operates similarly to the safety latch 286.

Similar to the body section 136, the body section 138 may include a pair of spaced apart guiding features 252 and 254. The guiding features 252 and 254 have a height 256 that projects away from the support surface 250. The guiding features 252 and 254 may also include respective mating edges 260 that engage the transfer board 122. In some embodiments, the mating edges 260 include rollers 265 that reduce friction between the transfer board 122 and the removable pallet 130. The rollers 265 may be aligned and spaced apart along the longitudinal axis 190. In the illustrated embodiment, the guiding features 252 and 254 are separate components that are attached to the body pad 246. However, in other embodiments, the guiding features 252 and 254 may be integrally formed with the body pad 246. The body section 138 may also include section ends 276 and 274. When the first and second body sections 136 and 138 are coupled together, the guiding features 212 and 214 of the first body section 136 may align with the guiding features 252 and 254. Furthermore, the support surfaces 210 and 250 may be substantially flush with respect to each other. The section ends 234 and 276 may abut each other. The support surfaces 210 and 250 may collectively form a pallet surface 450 (shown in FIG. 11). As such, the first and second body sections 136 and 138 may provide a substantially smooth transition from one body section to the other body section.

Figure 13:
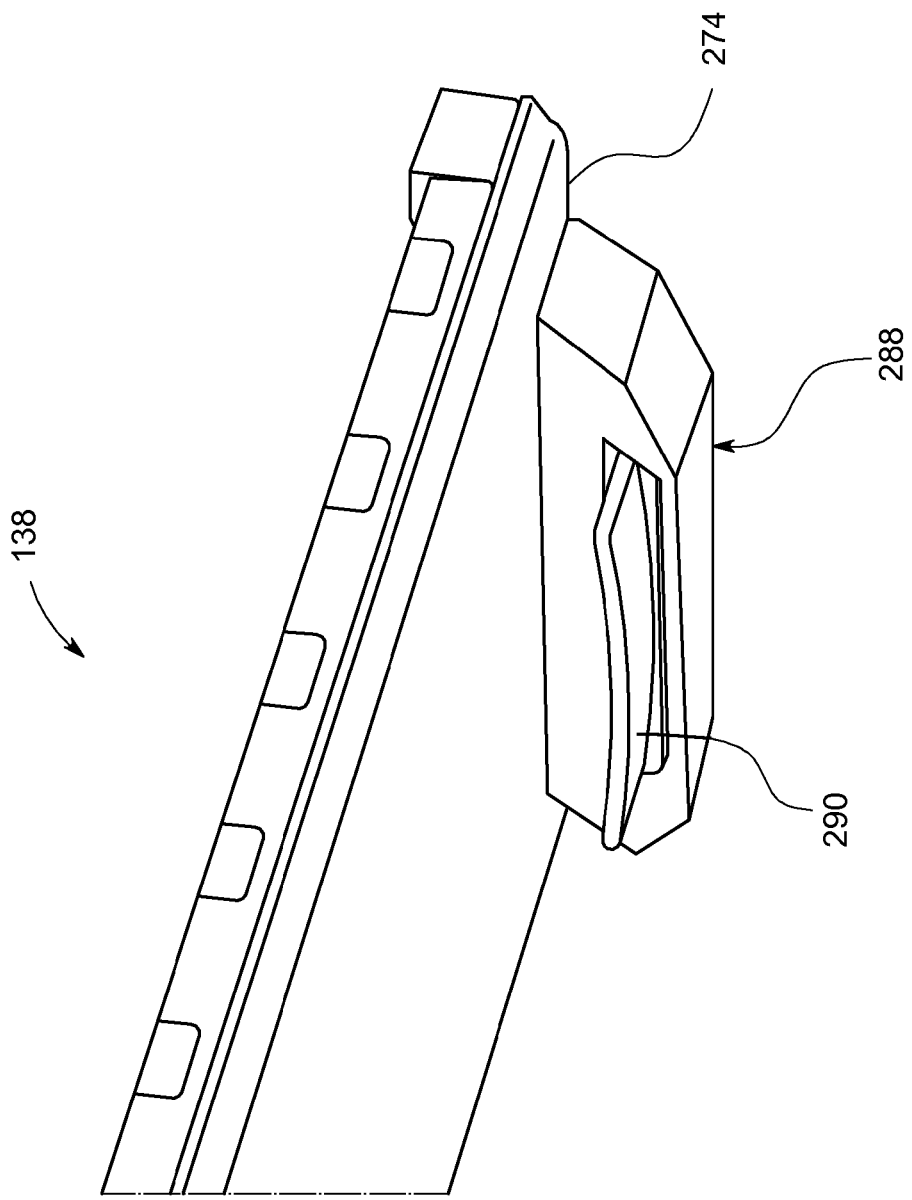
FIG. 13 is a bottom perspective view of the body section shown in FIG. 3.

FIG. 13 is a bottom perspective of the body section 138. As shown, the body section 138 may include a positioning device 288 located proximate to the section end 274. The positioning device 288 may be coupled to a bottom surface of the body section 138. The positioning device 288 includes a locking insert 290 that extends in an axial direction toward a front of the removable pallet 130. The locking insert 290 may be received by a similarly sized and shaped slot or cavity (not shown) of the patient table 120. The positioning device 288 may be used to facilitate positioning and locating the removable pallet 130 or, more specifically, the body section 138 in a desired position. Furthermore, at least a portion of the body section 138 may be located within the FOV 104 (FIG. 1). For example, the portion of the body section 138 shown in FIG. 13 may be located within the FOV 104. Accordingly, the body section 138 may include non-metallic materials or materials suitable for imaging, such as carbon fiber, foam, low-density plastic, and the like.

In some embodiments, the body sections 136 and 138 may comprise different materials. For example, the body pad 206 of the body section 136 may comprise a material that is configured for supporting the patient and the transfer board 122. However, the body pad 246 of the body section 138 may comprise a different material that is configured for improved image quality.

Figure 4:
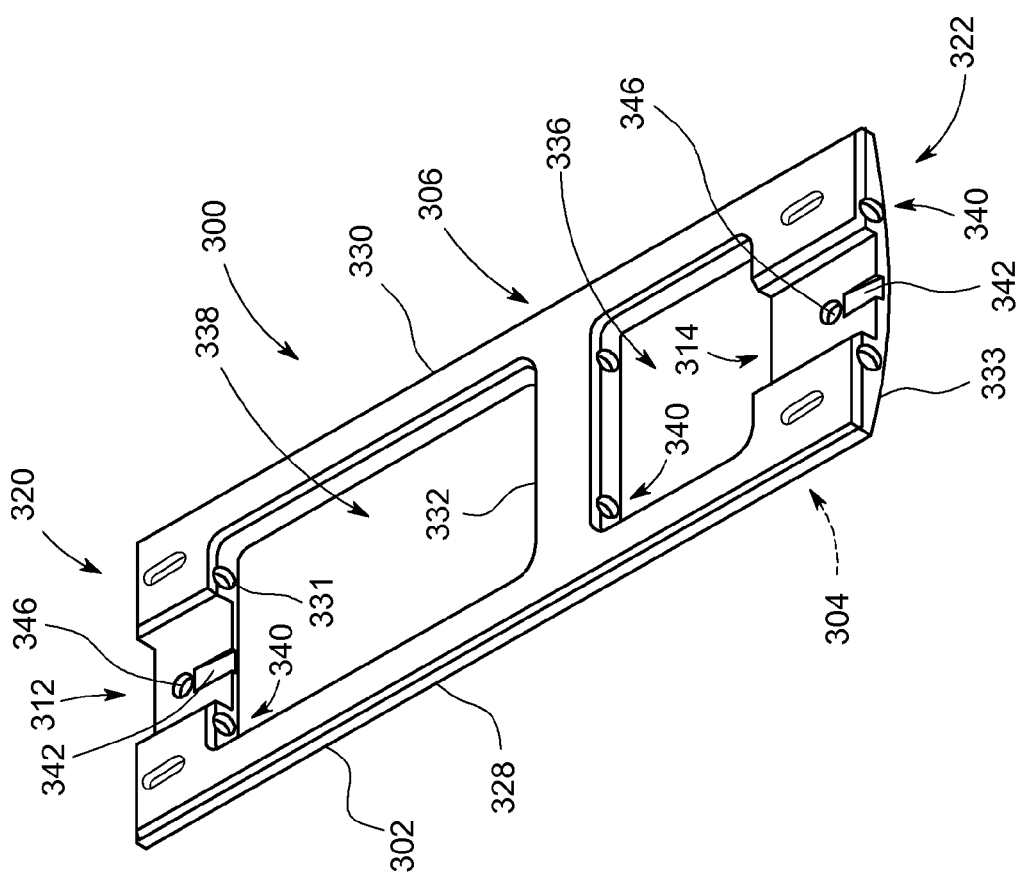
FIG. 4 is a perspective view of a coupling device that may be used to secure the removable pallet to a patient table.
Figure 5:
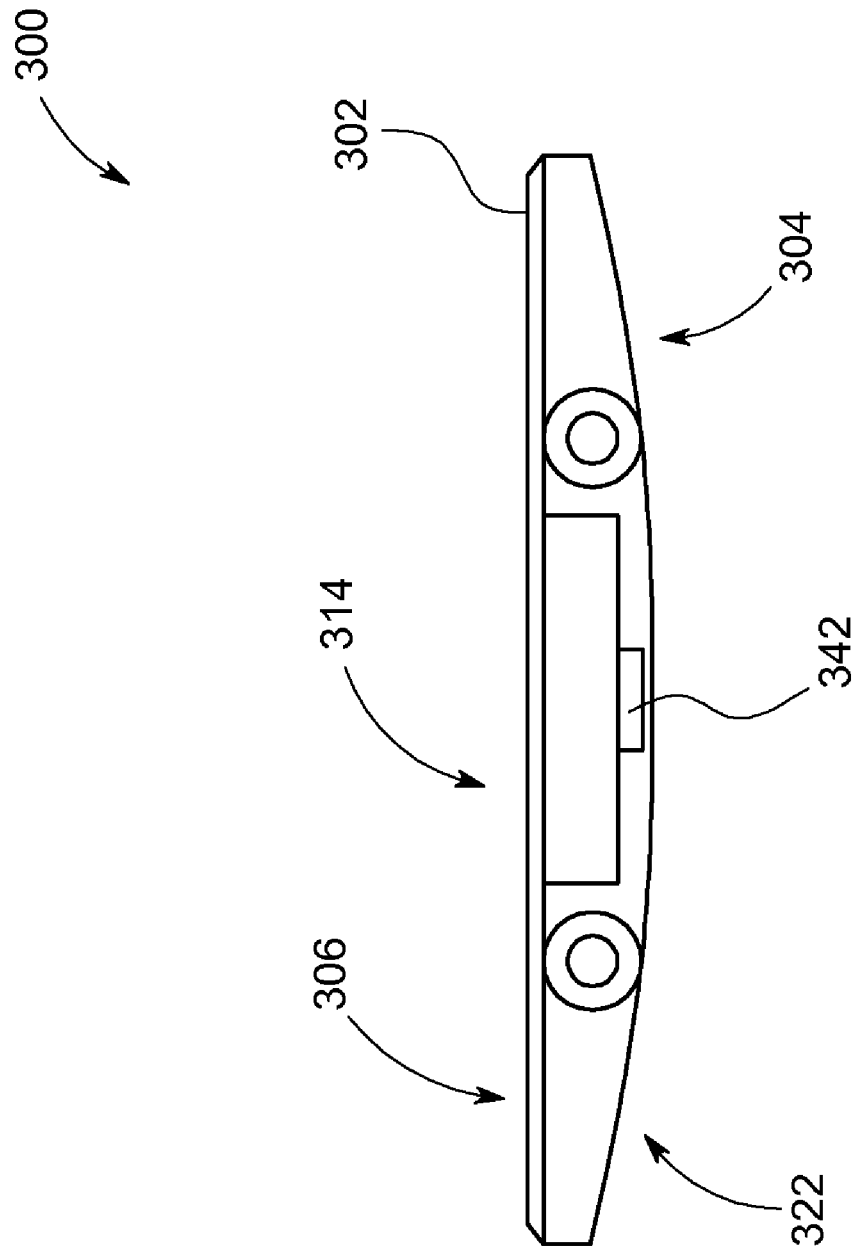
FIG. 5 is an end view of the coupling device shown in FIG. 4.

FIGS. 4 and 5 illustrate a perspective view and an end view, respectively, of a coupling member or device 300 that may be used to secure the removable pallet 130 to the patient table 120. As shown, the coupling device 300 has an elongated device body 302 that is configured to extend along the longitudinal axis 190 (FIG. 1) when mounted to the patient table 120 (FIG. 1). The coupling device 300 includes opposite ends 320 (FIG. 4) and 322. The coupling device 300 also includes a bottom surface 304 and a top surface 306. The bottom surface 304 is configured to engage the patient table 120. For example, the bottom surface 304 may have a contour or shape that complements a shape of a table surface 440 (shown in FIG. 11). The top surface 306 is configured to engage a mounting side or an underside 350 (shown in FIG. 6) of the removable pallet 130. For example, the top surface 306 may have a contour or shape that complements the underside.

Also shown in FIG. 4, the device body 302 may include a pair of elongated beams 328 and 330 that are joined by bridge elements 331-333. The elongated beams 328 and 330 may extend along the longitudinal axis 190 (FIG. 1) when the coupling device 300 is mounted to, for example, the cradle 442. The bridge elements 331-333 are separated by spacings 336 and 338. The device body 302 also includes slots 312 and 314 located proximate to the ends 320 and 322, respectively. In the illustrated embodiment, the slots 312 and 314 extend through the bridge elements 331 and 333, respectively. As will be described in greater detail below, the slots 312 and 314 are sized and shaped to receive features (e.g., mating units) of the removable pallet 130 to secure the removable pallet to the patient table 120. Also shown, the bridge elements 331-333 may include locating bores 340 and post holes 346.

Figure 6:
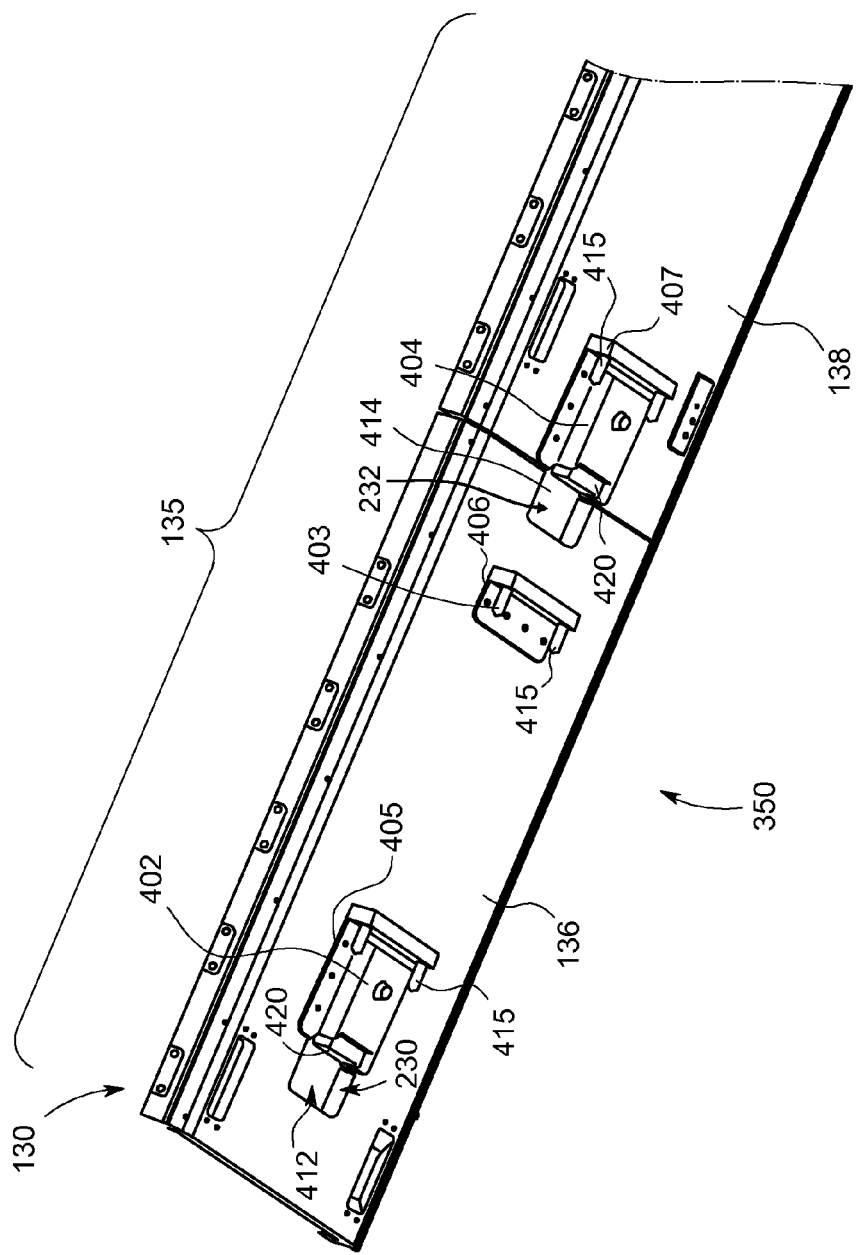
FIG. 6 is a bottom perspective view of the removable pallet before the removable pallet is mounted to the patient table.
Figure 7:
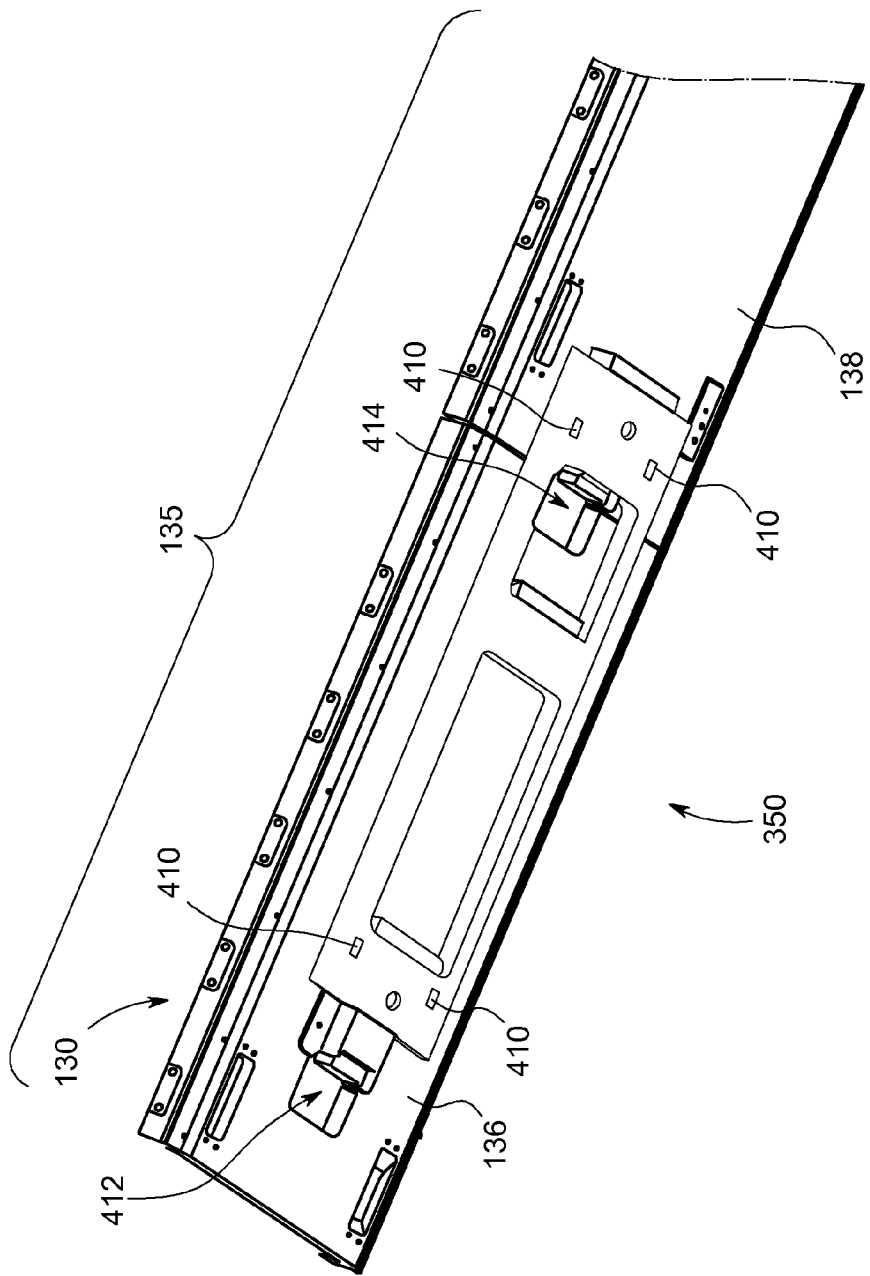
FIG. 7 is the bottom perspective view of the removable pallet shown in FIG. 6 in which the coupling device is engaged to the body sections.

FIGS. 6 and 7 show the underside 350 of the removable pallet 130 having the body sections 136 and 138 coupled together to form the support body 135. As described above, the removable pallet 130 may comprise multiple body sections or, alternatively, comprise a single elongated member or support body. FIG. 6 shows the removable pallet 130 without the coupling device 300 engaged thereto, and FIG. 7 shows the removable pallet 130 having the coupling device 300 removably engaged at the underside 350. In the exemplary embodiment, the coupling device 300 is coupled to (e.g., affixed to or removably coupled to) the cradle 442 (FIG. 9) of the patient table 120 before the body sections 136 and 138 are engaged with the coupling device 300. However, in alternative embodiments, the coupling device 300 may engage the body sections 136 and 138 as shown in FIG. 7 before the coupling device 300 engages the cradle 442.

By way of one example, the coupling device 300 may include mounting slots 410 (FIG. 7) that engage protrusions or pins (not shown) that project from the table surface 440 or the cradle 442. More specifically, the coupling device 300 may be positioned onto the cradle 442 so that the protrusions are inserted into the mounting slots 410. The coupling device 300 may then be moved in a locking direction (e.g., in a direction along the longitudinal axis) to engage the protrusions. The mounting slots 410 and the protrusions may also form an interference fit. In alternative embodiments, the cradle 442 (or table surface 440) may include the mounting slots and the coupling device may include protrusions.

In addition or alternatively to the above, the coupling device 300 may include fastener holes (not shown) that receive fasteners to affix the coupling device 300 to the patient table 120. When affixed to the patient table 120, the coupling device 300 may then removably engage the removable pallet 130. In other embodiments, the coupling device 300 may be affixed to the removable pallet 130. In such embodiments, the coupling device 300 may then removably engage the patient table 120. Yet in other embodiments, the coupling device 300 may removably engage the removable pallet 130 and the patient table 120. Furthermore, in some embodiments, the coupling device 300 is integrally formed with one of the patient table 120 and the removable pallet 130.

As shown in FIG. 6, the body sections 136 and 138 are coupled end-to-end such that section ends 234 and 276 abut each other along an interface. The removable pallet 130 may include one or more mating units, such as the mating units 402-404. In the illustrated embodiment, each body section 136 and 138 includes at least one mating unit. More specifically, the body section 136 includes the mating units 402 and 403 and the body section 138 includes the mating unit 404. As shown, the mating units 402-404 have housings 405-407, respectively. The housings 405 and 407 are sized and shaped to be inserted into the slots 312 and 314, respectively, of the coupling device 300. Furthermore, each housing 405-407 may include locating pins 415 that are sized and shaped to be inserted into the locating bores 340 (FIG. 4) of the coupling device 300. The locating pins 415 may project along the longitudinal axis 190 of the patient table 120. However, the illustrated embodiment is just one exemplary embodiment that demonstrates coupling the body sections 136 and 138. Variations or alternative embodiments may be used. For example, the locating pins and bores may have different positions or configurations. Furthermore, alternative mechanical means for coupling the body sections 136 and 138 may be used.

Figure 8:
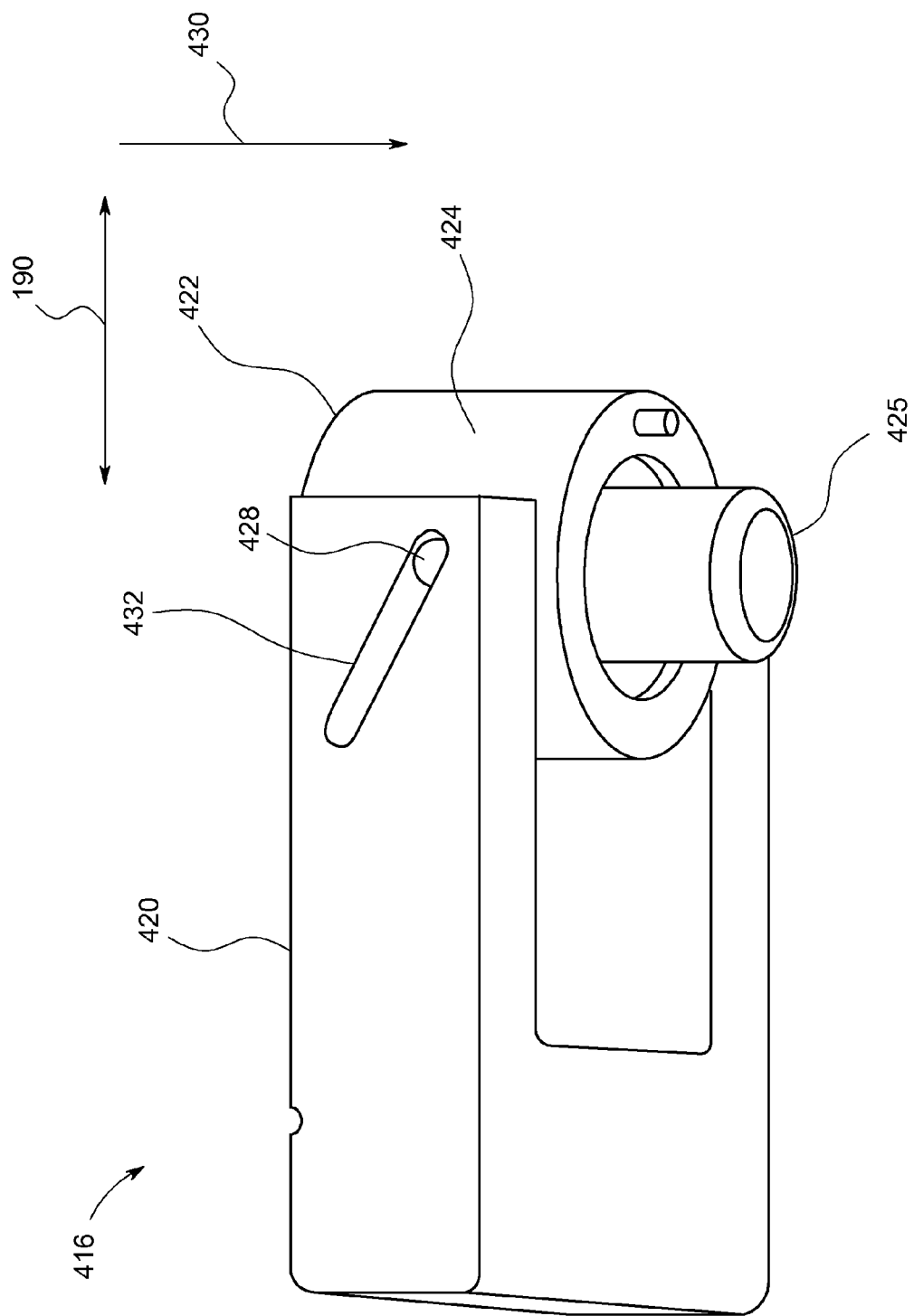
FIG. 8 is a perspective view of a locking mechanism that may be used with various embodiments.

FIG. 8 illustrates a locking mechanism 416 that may be used with the mating units, such as the mating units 402 and 404 (FIGS. 6 and 7). The locking mechanism 416 includes a trigger member 420 and a spring member 422 that are operatively coupled together. The spring member 422 includes a shell 424 having a post 425 biased by the spring member 422 and held within the shell 424. The post 425 is biased in a projected position as shown in FIG. 8 such that the spring member 422 provides a resilient force in a locking direction 430 that is substantially perpendicular to the longitudinal axis 190. The shell 424 may include one or more cam members 428 that extend into one or more grooves 432 of the trigger member 420. When the trigger member 420 is pushed in a direction along the longitudinal axis 190, the grooves 432 engage the cam members 428 to move the shell 424 in a direction that is opposite to the locking direction 430 (also called a release direction) thereby moving the post 425. When force on the trigger member 420 is removed, the potential energy stored within the spring member 422 moves the post 425 in the locking direction 430.

Returning to FIGS. 6 and 7, the hole 230 may form a body opening 412 of the support body 135 and the cut-out 232 (FIG. 3) may be closed off by the section end 276 (FIG. 3) to form a body opening 414. The mating units 402 and 404 may be located proximate to the body openings 412 and 414 so that the mating units 402 and 404 are accessible. In some embodiments, the body openings 412 and 414 are sized and shaped to permit a hand of an operator to reach therethrough and engage the trigger member 420 to release the corresponding body section.

Figure 9:
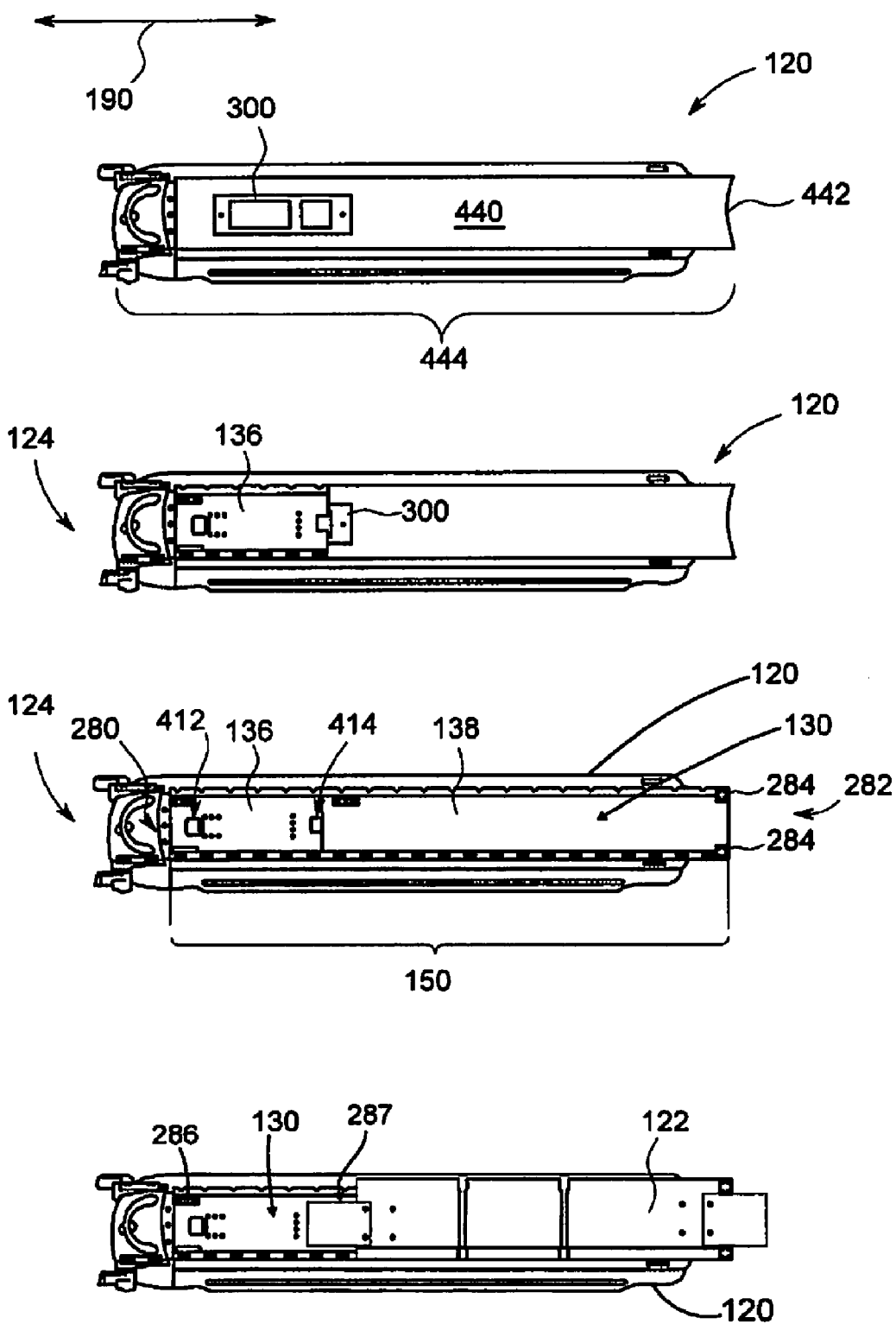
FIG. 9 is a series of side perspective views that illustrate the removable pallet being mounted to the patient table.
Figure 10:
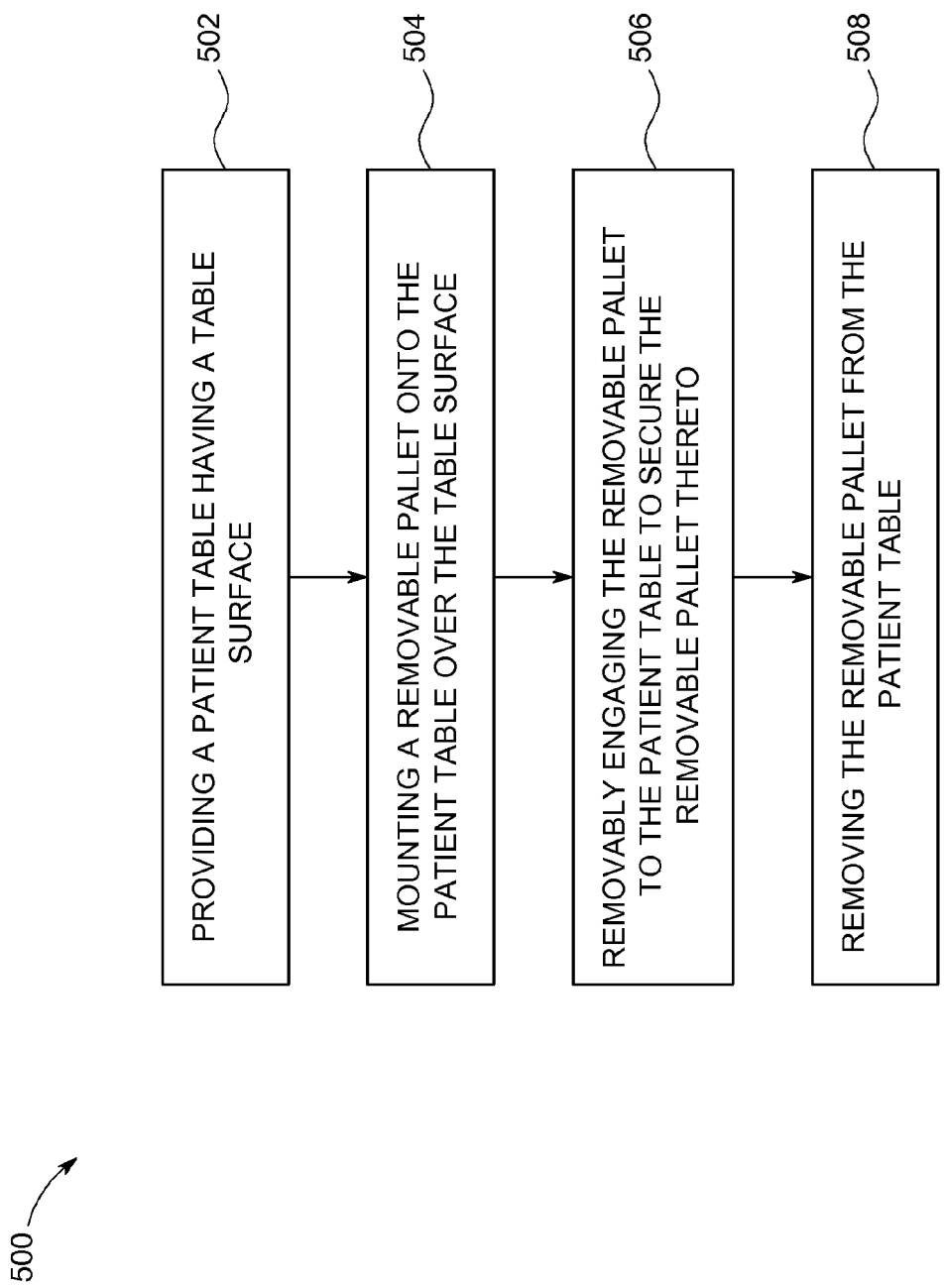
FIG. 10 is a block diagram illustrating a method of reconfiguring a patient table in accordance with various embodiments.

FIG. 9 illustrates a series of stages for reconfiguring a patient table 120 by mounting the removable pallet 130 thereto, and FIG. 10 is a block diagram of a method 500 of reconfiguring a patient table, such as the patient table 120 shown in FIG. 9. The following description of the method 500 is with respect to the series of assembly stages shown in FIG. 9. The method 500 includes providing at 502 the patient table 120. The patient table 120 has a table surface 440. In some embodiments, the patient table 120 may include a cradle 442 having the table surface 440. The cradle 442 may substantially extend along a length 444 of the patient table 120. In the illustrated embodiment, the patient table 120 may already include the coupling device 300 coupled to (e.g., removably engaged or affixed to) the patient table 120. In particular embodiments, the coupling device 300 is coupled to the cradle 442. However, in alternative embodiments, the coupling device 300 may be coupled to other components of the patient table 120 provided that the coupling device 300 may removably engage the removable pallet 130 as described herein.

The method 500 also includes mounting at 504 the removable pallet 130 onto the patient table 120. As shown, the removable pallet 130 may extend along the longitudinal axis 190 over the table surface 440 of the patient table 120. The method 500 also includes removably engaging 506 the removable pallet 130 to the coupling device 300. When the removable pallet 130 is removably engaged to the coupling device 300, the removable pallet 130 may be secured to the patient table 120.

In particular embodiments, the body sections 136 and 138 are coupled at separate times to the patient table 120 or to the coupling device 300. For example, the body section 136 may be positioned over the coupling device 300 such that the housing 405 of the mating unit 402 may be inserted or advanced into the slot 312 of the coupling device 300. The mating unit 403 may be positioned within the spacing 336 between the bridge elements 333 and 332. The locating pins 415 may be positioned to be inserted into the locating bores 340 of the bridge elements 332 and 331.

The body section 136 may then be moved in an axial direction along the longitudinal axis 190 toward the mating end 124 such that the locating pins 415 are advanced into the locating bores 340. As the body section 136 is moved in the axial direction, the post 425 of the spring member 422 of the mating unit 402 may engage the ramp surface 342 of the bridge element 331. The post 425 may resile (e.g., move away) from the bridge element 331 and slide therealong until the post 425 clears the post hole 346. At such time, the potential energy within the spring member 422 may project the post 425 into the post hole 346 thereby interlocking the body section 136 and the coupling device 300. During this time, the locating pins 415 of the mating unit 403 may be inserted into the locating bores 340 of the bridge element 332.

Similar to the body section 136, the body section 138 may be positioned over the coupling device 300 such that the housing 407 of the mating unit 404 may be inserted or advanced into the slot 314 of the coupling device 300. The locating pins 415 of the mating unit 404 may be positioned to be inserted into the locating bores 340 of the bridge element 333. Furthermore, the body section 138 may then be moved in an axial direction along the longitudinal axis 190 toward the mating end 124 such that the locating pins 415 are advanced into the locating bores 340. As the body section 138 is moved in the axial direction, the post 425 of the spring member 422 of the mating unit 404 may engage the ramp surface 342 of the bridge element 333. The post 425 may resile (e.g., move away) from the bridge element 333 and slide therealong until the post 425 clears the post hole 346. At such time, the potential energy within the spring member 422 may project the post 425 into the post hole 346 thereby interlocking the body section 138 and the coupling device 300. As such, the coupling device 300 may directly engage the body section 136 and the body section 138 to secure the removable pallet 130 to the patient table 120.

Accordingly, the first and second body sections 136 and 138 may be positioned end-to-end with respect to each other and secured to the patient table 120. The removable pallet 130 has a first or loading end 280 and a second or imaging end 282. As shown in FIG. 9, the removable pallet 130 includes the runway 150 that is configured to receive and slidably engage the transfer board 122 at the loading end 280. The runway 150 may direct or guide the transfer board 122 along the longitudinal axis 190 toward an axial location that may be, for example, proximate to the imaging end 282. Also shown in FIG. 9, the body sections 136 and 138 may include latches 286 and 287 that prevent the transfer board from being moved toward the mating end 124 after the transfer board 122 has cleared the latches.

Furthermore, embodiments described herein may be configured to direct the transfer board 122 to a predetermined location on the removable pallet 130. For example, the positive stops 284 located proximate to or at the imaging end 282 may be positioned to stop the transfer board 122 at the predetermined location. (The positive stops 284 are shown in FIGS. 3 and 9.) Accordingly, the removable pallet 130 may facilitate technicians repeatably locating the transfer board 122 on the removable pallet 130 at desired locations.

In addition, embodiments described herein may facilitate repeatably locating or positioning the removable pallet 130 on the patient table 120. For example, the body section 138 may include the positioning device 288. When in use, the positioning device 288, as shown in FIG. 13, may facilitate repeatably locating or positioning the body section 138 in a desired position. The positioning device 288 may engage or coupled to the bore end 126 (FIG. 1) of the patient table 120.

The method 500 may include removing or demounting at 508 the removable pallet 130 from the patient table 120. In particular embodiments, the demounting the removable pallet 130 may include removing the body section 138 by triggering the locking mechanism 416 of the mating unit 404. More specifically, a hand of an operator of the imaging system 100 or a tool may be inserted through the body opening 414 to engage the trigger member 420. The trigger member 420 may be moved in a trigger direction along the longitudinal axis 190. When the trigger member 420 is moved in the trigger direction, the post 425 is moved away from coupling device 300. The post 425 may be removed from the post hole 346. Once the locking mechanism 416 of the mating unit 404 is disengaged, the body section 138 may be moved in the axial direction away from the mating end 124 to remove the locating pins from the locating bores. The body section 138 may then be removed from the patient table 120.

The method 500 may also include demounting or removing the body section 136. In a similar manner as described above, the locking mechanism 416 of the mating unit 402 may be triggered by an operator or a tool through the body opening 412. Once the locking mechanism 416 of the mating unit 402 is disengaged, the body section 136 may be moved in the axial direction away from the mating end 124 to remove the locating pins from the locating bores. The body section 136 may then be removed from the patient table 120. The removable pallet 130 is no longer mounted to the patient table 120 and the patient table 120 may be used for a standard imaging session in which the patient independently mounts the patient table 120 or is picked up and placed onto the patient table 120.

Accordingly, a method of imaging may also be provided in which different imaging sessions are performed. A first imaging session may be performed without the removable pallet 130 and a second imaging session may be performed with the removable pallet mounted to the patient table 120 as described above.

Although the illustrated embodiment shows one particular method of mounting the removable pallet 130, alternative embodiments may include other mechanisms for securing and disengaging the removable pallet 130 or the body sections 136 and 138. For example, in one alternative embodiment, a removable pallet may include mating units similar to the mating units 402-404 that are coupled to edges of the removable pallet and project laterally away from the removable pallet. In such embodiments, the mating units may engage one or more coupling devices similar to the coupling device 300. The coupling device may be connected to a side of the patient table. As such, the coupling device is not required to be mounted to the cradle or the table surface.

Figure 11:
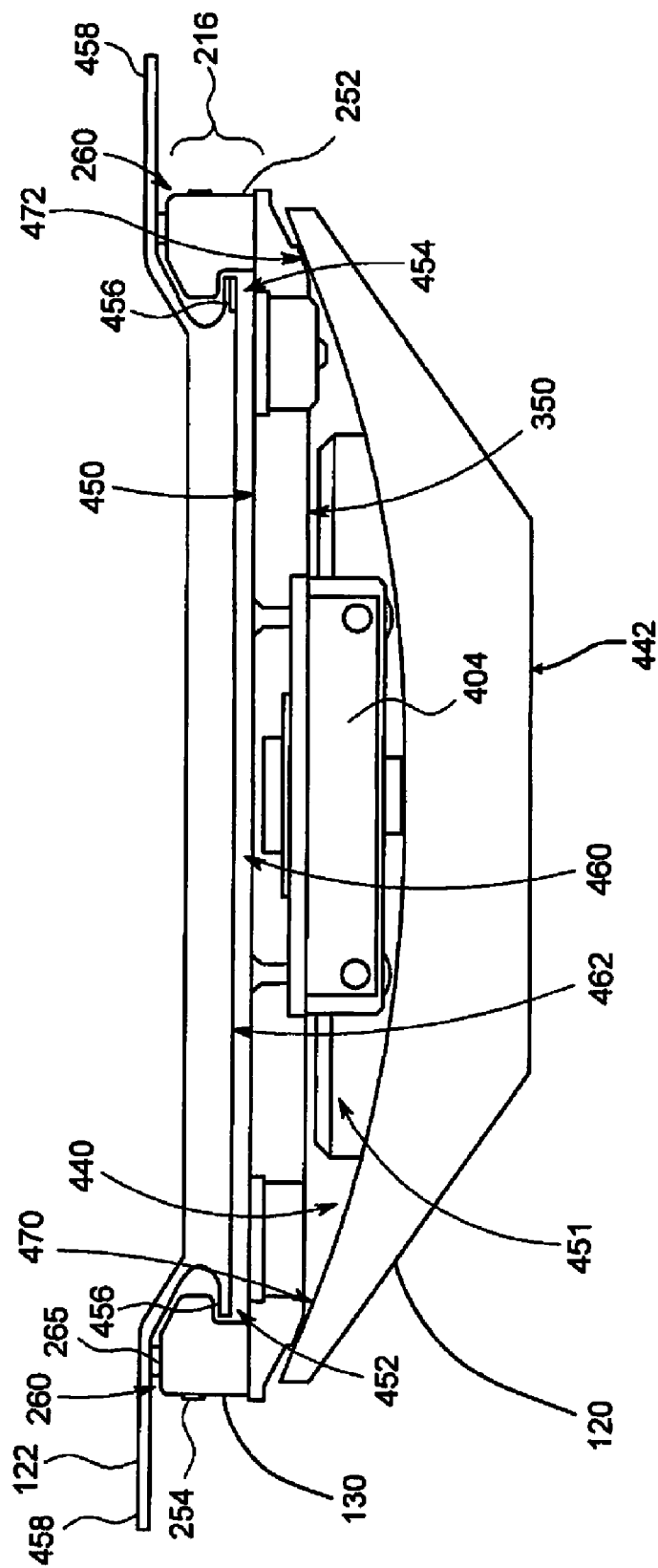
FIG. 11 is a cross-section of a portion of the patient table having the removable pallet and a transfer board thereon.

FIG. 11 shows a cross-section of a portion of the patient table 120 when the transfer board 122 is located on the body section 138. As shown, the patient table 120 may have a table surface 440 that is configured to hold a patient when the removable pallet 130 is not mounted to the patient table 120. The table surface 440 may have a cross-sectional contour, which is shown as being slightly concave. After the removable pallet 130 is mounted onto the patient table 120, the patient table 120 has a pallet surface 450. In the illustrated embodiment, the pallet surface 450 has a cross-sectional contour that is different than the cross-sectional contour of the table surface 440. In the illustrated embodiment, the pallet surface 450 is substantially planar. However, in alternative embodiments, the pallet and table surfaces 450 and 440 may have other cross-sectional contours. Furthermore, the cross-sectional contours may be substantially similar.

The removable pallet 130 may be supported by the coupling device 300 and lateral portions 470 and 472 proximate to the guiding features 254 and 252, respectively. The underside 350 may face the table surface 440 and extend substantially along an entire length of the patient table 120 over the table surface 440. When the removable pallet 130 is secured to the patient table 120, a spacing or gap 451 may exist between the table surface 440 and the underside 350 of the removable pallet 130. The gap 451 may provide space for the mating units 402-404.

Also shown in FIG. 11, the guiding features 252 and 254 project away from the pallet surface 450 by the height 216. Grip recesses 452 and 454 are formed within the guiding features 252 and 254, respectively, and are configured to receive guide fins 456 of the transfer board 122. The grip recesses 452 and 454 may also be configured to prevent the transfer board 122 from inadvertently leaving (e.g., jumping the guiding features 252 and 254) the removable pallet 130 during loading or unloading.

Furthermore, the transfer board 122 may include guide wings 458 that project laterally away from the transfer board 122 and are configured to engage the mating edges 260 of the removable pallet 130. As shown, the guide wings 458 engage the rollers 265. In the illustrated embodiment, when the transfer board 122 is moved along the removable pallet 130, a gap or spacing 460 exists between a bottom surface 462 of the transfer board 122 and the pallet surface 450. Accordingly, the removable pallet 130 enables the patient table 120 to be reconfigured when the patient table 120 is not compatible (or at least configured in a non-complementary manner) to engage a predetermined transfer board.

The runway 150 may be at least partially defined by the pallet surface 450 and the guiding features 252 and 254. The runway 150 is configured to direct the transfer board 122 along the patient table 120 to a desired position (e.g., axial location). Also shown in FIG. 11, the removable pallet 130 and, more specifically, the guiding features 252 and 254 may slidably engage the transfer board 122 and also provide free access to the transfer board 122 from above a top surface of the transfer board 122. As such, various accessories, such as arm or leg belts, headrests, body straps, and others, may be freely coupled to the transfer board 122.

Figure 12:
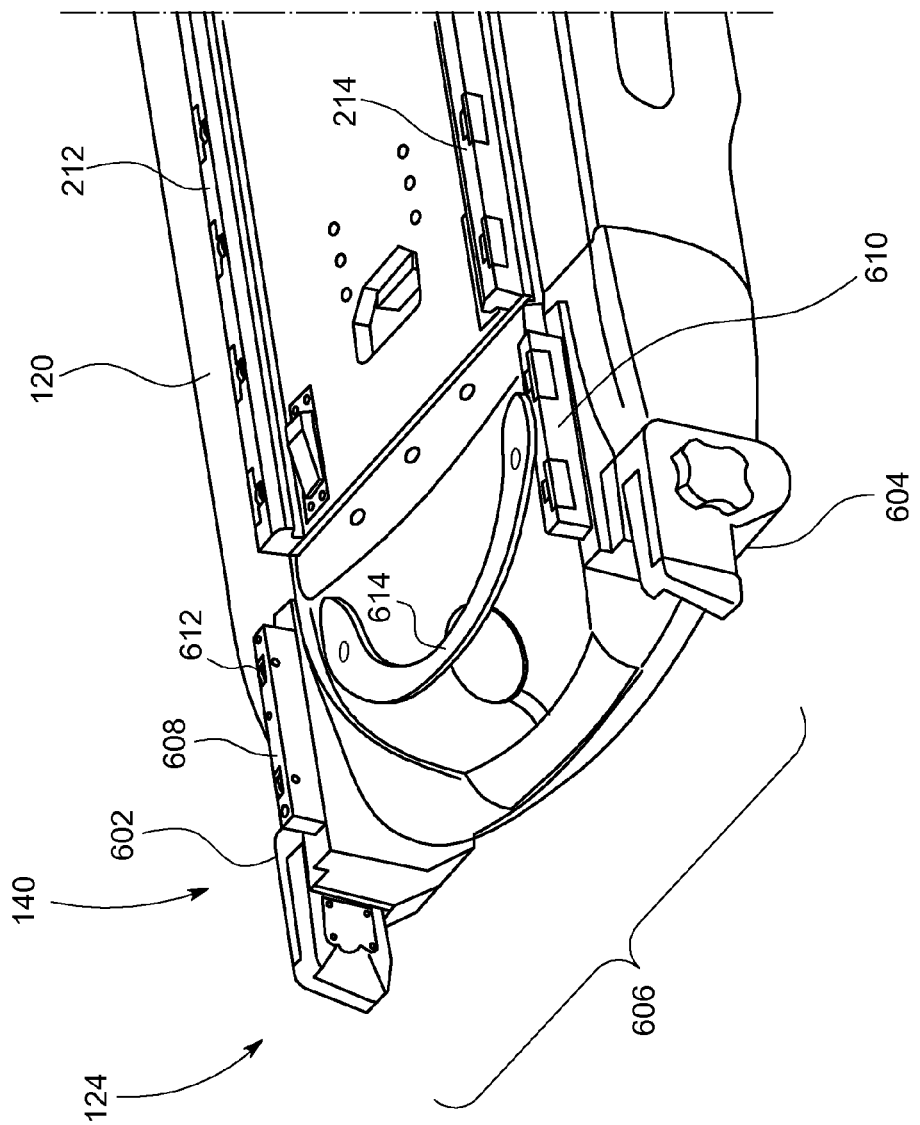
FIG. 12 is a perspective view of a docking interface that may be used in accordance with various embodiments.

FIG. 12 is a perspective view of the docking interface 140. The docking interface 140 includes at least one transporter engagement device that removably engages the transporter 132 (FIG. 1) to prevent the transporter 132 from moving away (e.g., inadvertently moving away) from the patient table 120 during the transfer of a patient. More specifically, the docking interface 140 may include a pair of engagement devices 602 and 604 that are spaced apart along a width 606 of the mating end 124. Also shown, the docking interface 140 may include spaced apart guiding features 608 and 610 that are similar to the guiding features 212 and 214. The guiding features 608 and 610 may also include rollers 612 that engage the transfer board 122 when the transfer board 122 is removed from the transporter 132. The guiding features 608 and 610 and the guiding features 212 and 214 may be positioned relative to each other to facilitate a smooth transfer of the transfer board 122 between the patient table 120 and the transporter 132. Also shown, the docking interface 140 or the patient table 120 may include a handle 614 located at the mating end 124 of the patient table 120. The handle 614 may be shaped to permit the transfer board 122 to slide over the handle 614.

In the illustrated embodiment, the docking interface 140 is separately connected to the patient table 120. However, in alternative embodiments, the docking interface 140 may be integrally formed with the removable pallet 130. For example, the docking interface 140 may be integrally formed with the body section 136.

It is to be understood that the above description is intended to be illustrative, and not restrictive. For example, the above described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A removable pallet for mounting to a patient table, the patient table having a table surface adapted to support patients thereon, the removable pallet comprising:
   a support body having a runway configured to slidably engage a transfer board carrying a patient, the support body extending along a longitudinal axis and configured to be mounted over the table surface of the patient table; and
   a coupling device configured to removably couple the support body and the patient table, wherein the coupling device secures the support body over the table surface to permit the transfer board to be moved onto the patient table;
   wherein the support body includes an underside that faces the table surface when the support body is secured to the patient table, the coupling device extending from the underside to the table surface of the patient table.

2. The removable pallet in accordance with claim 1 wherein the support body includes at least one guiding feature extending along the runway in a direction along the longitudinal axis, the guiding feature being configured to engage the transfer board to facilitate directing the transfer board to an axial location.

3. The removable pallet in accordance with claim 1 wherein the coupling device is configured to be coupled to the patient table such that the coupling device remains coupled to the patient table when the support body is demounted from the patient table.

4. The removable pallet in accordance with claim 1 wherein the support body includes a locking mechanism that engages the coupling device.

5. The removable pallet in accordance with claim 4 wherein the support body includes a body opening through the runway, the body opening located proximate to the locking mechanism to provide access to the locking mechanism for an operator or tool, the support body being removable when the locking mechanism is triggered by the operator or tool.

6. The removable pallet in accordance with claim 1 wherein the coupling device is removably engaged to the support body such that the support body is readily separable from a top surface of the coupling device.

7. The removable pallet in accordance with claim 1 wherein the coupling device is removably engaged to the patient table.

8. The removable pallet in accordance with claim 1 wherein the coupling device is integrally formed with one of the patient table and the support body.

9. The removable pallet in accordance with claim 1 further comprising a docking interface configured to removably engage a transporter at a mating end of the patient table.

10. The removable pallet in accordance with claim 1 wherein the support body comprises a plurality of separable body sections, the body sections configured to couple together to form the runway, the body sections having respective bottom surfaces that face the table surface and form at least a portion of the underside.

11. The removable pallet in accordance with claim 10 wherein the coupling device directly and removably engages at least two of the body sections to secure the support body to the patient table.

12. The removable pallet in accordance with claim 10 wherein at least two of the body sections comprise different body materials.

13. The removable pallet in accordance with claim 10 wherein at least two of the body sections are configured to be coupled to the coupling device at separate times.

14. A method of reconfiguring a patient table, the method comprising:
   providing a patient table that extends along a longitudinal axis;
   mounting a removable pallet onto the patient table, the removable pallet extending along the longitudinal axis over a table surface that is adapted to hold a patient thereon; and
   removably engaging the removable pallet to the patient table, the removable pallet having a runway configured to slidably engage a transfer board having a patient thereon, wherein the removably engaging includes positioning a coupling device between the patient table and an underside of the removable pallet, the coupling device configured to removably couple the patient table and the removable pallet so that the removable pallet is secured over the table surface;
   wherein the removable pallet comprises first and second separable body sections, the body sections having respective bottom surfaces that face the table surface and form at least a portion of the underside of the removable pallet, and wherein the removably engaging the removable pallet includes securing the first and second sections to the coupling device at separate times.

15. The method in accordance with claim 14 wherein the coupling device is affixed to one of the patient table and the removable pallet.

16. The method in accordance with claim 14 wherein the removable pallet includes at least one body opening that provides access to at least one locking mechanism, the locking mechanism securing the removable pallet to the patient table, the method further comprising triggering the locking mechanism to release the removable pallet.

17. A reconfigurable imaging table for a medical imaging system, the imaging table comprising:
   a cradle having a table surface extending along a longitudinal axis, the table surface adapted to support a patient thereon during an imaging session;

a removable pallet configured to be mounted to the cradle, the removable pallet having a runway configured to slidably engage a transfer board, the removable pallet extending along the longitudinal axis when mounted to the cradle; and a coupling device coupled to the removable pallet, the coupling device configured to removably couple the removable pallet and the cradle, wherein the coupling device secures the removable pallet to the cradle to allow the transfer board to be moved onto the runway of the removable pallet;

wherein the removable pallet includes an underside that faces the table surface when the removable pallet is secured to the cradle, the coupling device extending from the underside of the removable pallet to the table surface of the cradle.

18. A removable pallet for mounting to a patient table, the patient table having a table surface adapted to support patients thereon, the removable pallet comprising:

a support body having a runway configured to slidably engage a transfer board carrying a patient, the support body extending along a longitudinal axis and configured to be mounted over the table surface, the support body comprising a plurality of separable body sections coupled together to form the runway; and a coupling device configured to removably couple the support body and the patient table, wherein the coupling device removably couples to at least two of the body sections to secure the support body over the table surface, the body sections having bottom surfaces that form at least a portion of an underside of the support body, the underside facing the table surface.

19. The removable pallet in accordance with claim 18 wherein at least two of the body sections are held end-to-end such that ends of the at least two body sections abut each other along an interface.

* * * * *

UNITED STATES PATENT AND TRADEMARK OFFICE
CERTIFICATE OF CORRECTION

| | | |
|---|---|---|
| PATENT NO. | : 8,166,586 B2 | Page 1 of 1 |
| APPLICATION NO. | : 12/641558 | |
| DATED | : May 1, 2012 | |
| INVENTOR(S) | : Bridge et al. | |

It is certified that error appears in the above-identified patent and that said Letters Patent is hereby corrected as shown below:

In Column 3, Line 20, delete "(MM)" and insert -- (MRI) --, therefor.

In Column 14, Lines 55-56, delete "one of the patient table and the removable pallet." and insert -- the patient table. --, therefor.

In Column 14, Line 60, delete "mechanism" and insert -- mechanism engaging the coupling device and --, therefor.

Signed and Sealed this
Twenty-seventh Day of November, 2012

David J. Kappos
*Director of the United States Patent and Trademark Office*